US012741918B2

(12) United States Patent
Suzuki

(10) Patent No.: US 12,741,918 B2
(45) **Date of Patent: *Sep. 22, 2026**

(54) METHOD FOR STORING FLUOROBUTENE

(71) Applicant: Resonac Corporation, Tokyo (JP)

(72) Inventor: Atsushi Suzuki, Tokyo (JP)

(73) Assignee: Resonac Corporation, Tokyo (JP)

( * ) Notice: Subject to any disclaimer, the term of this patent is extended or adjusted under 35 U.S.C. 154(b) by 588 days.

This patent is subject to a terminal disclaimer.

(21) Appl. No.: 18/031,460

(22) PCT Filed: Oct. 8, 2021

(86) PCT No.: PCT/JP2021/037423

§ 371 (c)(1),
(2) Date: Apr. 12, 2023

(87) PCT Pub. No.: WO2022/080269

PCT Pub. Date: Apr. 21, 2022

(65) Prior Publication Data

US 2024/0018075 A1 Jan. 18, 2024

(30) Foreign Application Priority Data

Oct. 15, 2020 (JP) ................................ 2020-173916

(51) Int. Cl.
*C07C 21/18* (2006.01)

(52) U.S. Cl.
CPC .................................. *C07C 21/18* (2013.01)

(58) Field of Classification Search
CPC ................................ C07C 21/18; C07C 17/38
See application file for complete search history.

(56) References Cited

U.S. PATENT DOCUMENTS

| | | | |
|---|---|---|---|
| 5,516,951 | A | 5/1996 | Aoyama |
| 8,461,401 | B2 | 6/2013 | Tung et al. |
| 10,077,330 | B2 | 9/2018 | Van Der Puy et al. |
| 10,457,866 | B2 | 10/2019 | Nakamura et al. |
| 10,941,237 | B2 | 3/2021 | Van Der Puy et al. |
| 2005/0119512 | A1 | 6/2005 | Du et al. |
| 2007/0265478 | A1 | 11/2007 | Ji et al. |
| 2010/0264116 | A1 | 10/2010 | Suzuki et al. |
| 2011/0237844 | A1 | 9/2011 | Tung et al. |
| 2011/0282023 | A1 | 11/2011 | Johnson et al. |
| 2012/0004475 | A1 | 1/2012 | Miller et al. |
| 2012/0220135 | A1 | 8/2012 | Nakagawa et al. |
| 2012/0323054 | A1 | 12/2012 | Knapp |
| 2013/0090439 | A1 | 4/2013 | Lu et al. |
| 2015/0051426 | A1 | 2/2015 | Fukushima et al. |
| 2015/0294880 | A1 | 10/2015 | Anderson et al. |
| 2016/0009847 | A1 | 1/2016 | Van Der Puy et al. |
| 2017/0015607 | A1 | 1/2017 | Baldychev et al. |
| 2017/0103901 | A1 | 4/2017 | Shen et al. |
| 2017/0110336 | A1 | 4/2017 | Hsu et al. |
| 2018/0066187 | A1 | 3/2018 | Nakamura et al. |
| 2018/0215979 | A1 | 8/2018 | Kontomaris |
| 2019/0031582 | A1 | 1/2019 | Peng |
| 2019/0085115 | A1 | 3/2019 | Van Der Puy et al. |

FOREIGN PATENT DOCUMENTS

| | | | |
|---|---|---|---|
| CN | 102884030 | A | 1/2013 |
| CN | 103958553 | A | 7/2014 |
| CN | 105008442 | A | 10/2015 |
| CN | 107533969 | A | 1/2018 |
| CN | 108727154 | A | 11/2018 |
| CN | 108911947 | A | 11/2018 |
| EP | 3 238 820 | A1 | 11/2017 |
| JP | 2945927 | B | 9/1999 |
| JP | 2000-038356 | A | 2/2000 |
| JP | 2006-525339 | A | 11/2006 |
| JP | 2008-81477 | A | 4/2008 |
| JP | 2010-1244 | A | 1/2010 |
| JP | 2011-136955 | A | 7/2011 |
| JP | 2012-512859 | A | 6/2012 |
| JP | 2012-131731 | A | 7/2012 |
| JP | 2012-195576 | A | 10/2012 |
| JP | 2017-92357 | A | 5/2017 |
| JP | 2018-529872 | A | 10/2018 |
| JP | 6451810 | B2 | 1/2019 |
| JP | 2019-034972 | A | 3/2019 |
| JP | 2020-528917 | A | 10/2020 |
| WO | 94/12454 | A1 | 6/1994 |
| WO | 2020/170980 | A1 | 8/2020 |

OTHER PUBLICATIONS

Opteon® 1100 Catalog, 2016, The Chemours Company, LLC.
Opteon® SF33 Catalog, 2018, The Chemours Company, LLC.

*Primary Examiner* — Jafar F Parsa
(74) *Attorney, Agent, or Firm* — Sughrue Mion, PLLC

(57) ABSTRACT

Provided is a method for storing a fluorobutene by which polymerization is unlikely to proceed during storage. A fluorobutene represented by general formula $C_4H_xF_y$ where x is 0 or more and 7 or less, y is 1 or more and 8 or less, and x+y is 8 contains or does not contain at least one of sodium, potassium, magnesium, and calcium as a metal impurity. The fluorobutene is stored in a container in which the total concentration of sodium, potassium, magnesium, and calcium is 1,000 ppb by mass or less when containing at least one of sodium, potassium, magnesium, and calcium.

7 Claims, No Drawings

METHOD FOR STORING FLUOROBUTENE

CROSS REFERENCE TO RELATED APPLICATIONS

This application is a National Stage of International Application No. PCT/JP2021/037423, filed Oct. 8, 2021, claiming priority to Japanese Patent Application No. 2020-173916, filed Oct. 15, 2020.

TECHNICAL FIELD

The present invention relates to a method for storing a fluorobutene.

BACKGROUND ART

Unsaturated fluorocarbons disclosed, for example, in PTLs 1 and 2 may be used as an etching gas for dry etching.

CITATION LIST

Patent Literature

PTL 1: JP 6451810 B
PTL 2: JP 2019-034972 A

SUMMARY OF INVENTION

Technical Problem

Unsaturated fluorocarbons are, however, easily polymerized through reaction of unsaturated bonds, and the polymerization may proceed during storage for a long time to reduce the purity.

The present invention is intended to provide a method for storing a fluorobutene by which polymerization is unlikely to proceed during storage.

Solution to Problem

To solve the problems, aspects of the present invention are the following [1] to [4].

[1] A method for storing a fluorobutene represented by general formula $C_4H_xF_y$ where x is 0 or more and 7 or less, y is 1 or more and 8 or less, and x+y is 8, in which the fluorobutene contains or does not contain at least one of sodium, potassium, magnesium, and calcium as a metal impurity, and the fluorobutene is stored in a container in which the total concentration of sodium, potassium, magnesium, and calcium is 1,000 ppb by mass or less when the fluorobutene contains at least one of sodium, potassium, magnesium, and calcium.

[2] The method for storing a fluorobutene according to the aspect [1], in which the fluorobutene further contains or does not contain at least one of manganese, cobalt, nickel, and silicon as the metal impurity, and the fluorobutene is stored in a container in which the sum total concentration of sodium, potassium, magnesium, calcium, manganese, cobalt, nickel, and silicon is 2,000 ppb by mass or less when the fluorobutene further contains at least one of manganese, cobalt, nickel, and silicon.

[3] The method for storing a fluorobutene according to the aspect [1] or [2], in which the fluorobutene is at least one selected from 1,1,1,4,4,4-hexafluoro-2-butene, 1,1,1,2,4,4,4-heptafluoro-2-butene, 3,3,4,4,4-pentafluoro-1-butene, and 2,3,3,4,4,4-hexafluoro-1-butene.

[4] The method for storing a fluorobutene according to any one of the aspects [1] to [3], in which the fluorobutene is stored at a temperature of −20° C. or more and 50° C. or less.

Advantageous Effects of Invention

According to the present invention, a fluorobutene is unlikely to be polymerized during storage.

DESCRIPTION OF EMBODIMENTS

Embodiments of the present invention will now be described. The embodiments are merely examples of the present invention, and the present invention is not limited to the embodiments. Various modifications or improvements can be made in the embodiments, and such modifications and improvements can be encompassed by the present invention.

The method for storing a fluorobutene pertaining to the present embodiment is a method for storing a fluorobutene represented by general formula $C_4H_xF_y$ where x is 0 or more and 7 or less, y is 1 or more and 8 or less, and x+y is 8. In the method, the fluorobutene contains or does not contain at least one of sodium (Na), potassium (K), magnesium (Mg), and calcium (Ca) as a metal impurity, and the fluorobutene is stored in a container in which the total concentration of sodium, potassium, magnesium, and calcium is 1,000 ppb by mass or less when the fluorobutene contains at least one of sodium, potassium, magnesium, and calcium.

When a fluorobutene contains at least one of sodium, potassium, magnesium, and calcium as a metal impurity, the catalytic action of the metal impurity accelerates polymerization reaction of carbon-carbon double bonds in the fluorobutene. Hence, a fluorobutene containing a metal impurity may be polymerized during storage, and the purity may decrease.

A fluorobutene stored by the method for storing a fluorobutene pertaining to the present embodiment contains no metal impurity or contains a metal impurity at a small content and thus is unlikely to be polymerized even when stored for a long time, and the purity is unlikely to decrease. Accordingly, the fluorobutene can be stably stored over a long time without containing any polymerization inhibitor that suppresses polymerization of the fluorobutene.

The technology disclosed in PTLs 1 and 2 does not consider the concentration of a metal impurity in an unsaturated fluorocarbon. Hence, when an unsaturated fluorocarbon is stored by the technology disclosed in PTLs 1 and 2, a metal impurity may accelerate polymerization reaction of carbon-carbon double bonds in the unsaturated fluorocarbon. As a result, the unsaturated fluorocarbon may be polymerized during storage, and the purity may decrease.

Hereinafter, the method for storing a fluorobutene pertaining to the present embodiment will be described in further detail.

[Fluorobutene]

The fluorobutene pertaining to the present embodiment is represented by general formula $C_4H_xF_y$ and satisfies three requirements in the general formula: x is 0 or more and 7 or less; y is 1 or more and 8 or less; and x+y is 8. The fluorobutene may be any type that satisfies the above requirements and may be either a linear fluorobutene or a branched fluorobutene (isobutene) but is preferably a fluoro-1-butene or a fluoro-2-butene.

Specific examples of the fluoro-1-butene include $CHF_2$—$CF_2$—CF═$CF_2$, $CF_3$—$CF_2$—CF═CHF, $CF_3$—CHF—

CF=$CF_2$, $CF_3$—$CF_2$—CH=$CF_2$, $CHF_2$—CHF—CF=$CF_2$, $CHF_2$—$CF_2$—CF=CHF, $CF_3$—CHF—CF=CHF, $CF_3$—$CF_2$—CH=CHF, $CF_3$—CHF—CH=$CF_2$, $CHF_2$—$CF_2$—CH=$CF_2$, $CH_3$—$CF_2$—CF=$CF_2$, $CH_2F$—CHF—CF=$CF_2$, $CH_2F$—$CF_2$—CH=$CF_2$, $CH_2F$—$CF_2$—CF=CHF, $CHF_2$—$CH_2$—CF=$CF_2$, $CHF_2$—CHF—CH=$CF_2$, $CHF_2$—CHF—CF=CHF, $CHF_2$—$CF_2$—CH=CHF, $CHF_2$—$CF_2$—CF=$CH_2$, $CF_3$—$CH_2$—CH=$CF_2$, $CF_3$—$CH_2$—CF=CHF, $CF_3$—CHF—CH=CHF, $CF_3$—CHF—CF=$CH_2$, $CF_3$—$CF_2$—CH=$CH_2$, $CH_3$—CHF—CF=$CF_2$, $CH_3$—$CF_2$—CH=$CF_2$, $CH_3$—$CF_2$—CF=CHF, $CH_2F$—$CH_2$—CF=$CF_2$, $CH_2F$—CHF—CH=$CF_2$, $CH_2F$—CHF—CF=CHF, $CH_2F$—$CF_2$—CH=CHF, $CH_2F$—$CF_2$—CF=$CH_2$, $CHF_2$—$CH_2$—CH=$CF_2$, $CHF_2$—$CH_2$—CF=CHF, $CHF_2$—CHF—CH=CHF, $CHF_2$—CHF—CF=$CH_2$, $CHF_2$—$CF_2$—CH=$CH_2$, $CF_3$—$CH_2$—CH=CHF, $CF_3$—$CH_2$—CF=$CH_2$, $CF_3$—CHF—CH=$CH_2$, $CH_3$—$CH_2$—CF=$CF_2$, $CH_3$—CHF—CH=$CF_2$, $CH_3$—CHF—CF=CHF, $CH_3$—$CF_2$—CH=CHF, $CH_3$—$CF_2$—CF=$CH_2$, $CH_2F$—$CH_2$—CH=$CF_2$, $CH_2F$—$CH_2$—CF=CHF, $CH_2F$—CHF—CH=CHF, $CH_2F$—CHF—CF=$CH_2$, $CH_2F$—$CF_2$—CH=$CH_2$, $CHF_2$—$CH_2$—CH=CHF, $CHF_2$—$CH_2$—CF=$CH_2$, $CHF_2$—CHF—CH=$CH_2$, $CF_3$—$CH_2$—CH=$CH_2$, $CH_3$—$CH_2$—CH=$CF_2$, $CH_3$—$CH_2$—CF=CHF, $CH_3$—CHF—CH=CHF, $CH_3$—CHF—CF=$CH_2$, $CH_3$—$CF_2$—CH=$CH_2$, $CH_2F$—$CH_2$—CH=CHF, $CH_2F$—$CH_2$—CF=$CH_2$, $CH_2F$—CHF—CH=$CH_2$, $CHF_2$—$CH_2$—CH=$CH_2$, $CH_3$—$CH_2$—CH=CHF, $CH_3$—$CH_2$—CF=$CH_2$, $CH_3$—CHF—CH=$CH_2$, and $CH_2F$—$CH_2$—CH=$CH_2$.

Specific examples of the fluoro-2-butene include $CHF_2$—CF=CF—$CF_3$, $CF_3$—CH=CF—$CF_3$, $CH_2F$—CF=CF—$CF_3$, $CHF_2$—CH=CF—$CF_3$, $CHF_2$—CF=CF—$CHF_2$, $CF_3$—CH=CH—$CF_3$, $CH_3$—CF=CF—$CF_3$, $CH_2F$—CH=CF—$CF_3$, $CH_2F$—CF=CH—$CF_3$, $CH_2F$—CF=CF—$CHF_2$, $CHF_2$—CH=CH—$CF_3$, $CHF_2$—CF=CH—$CHF_2$, $CH_3$—CH=CF—$CF_3$, $CH_3$—CF=CH—$CF_3$, $CH_3$—CF=CF—$CHF_2$, $CH_2F$—CH=CH—$CF_3$, $CH_2F$—CH=CF—$CHF_2$, $CH_2F$—CF=CH—$CHF_2$, $CH_2F$—CF=CF—$CH_2F$, $CHF_2$—CH=CH—$CHF_2$, $CH_3$—CH=CH—$CF_3$, $CH_3$—CH=CF—$CHF_2$, $CH_3$—CF=CH—$CHF_2$, $CH_3$—CF=CF—$CH_2F$, $CH_2F$—CF=CH—$CH_2F$, $CH_2F$—CH=CH—$CHF_2$, $CH_3$—CH=CH—$CHF_2$, $CH_3$—CH=CF—$CH_2F$, $CH_3$—CF=CH—$CH_2F$, $CH_3$—CF=CF—$CH_3$, $CH_2F$—CH=CH—$CH_2F$, $CH_3$—CH=CH—$CH_2F$, and $CH_3$—CH=CF—$CH_3$.

These fluorobutenes may be used singly or in combination of two or more of them. Some of the fluorobutenes have cis-trans isomers, and both cis- and trans-fluorobutenes can be used in the method for storing a fluorobutene pertaining to the present embodiment.

When a fluorobutene is stored in a container, a gas consisting only of the fluorobutene may be stored in a container, or a mixed gas containing the fluorobutene and a dilution gas may be stored in a container. As the dilution gas, at least one gas selected from nitrogen gas ($N_2$), helium (He), neon (Ne), argon (Ar), krypton (Kr), and xenon (Xe) can be used. The content of the dilution gas is preferably 90% by volume or less and more preferably 50% by volume or less relative to the total volume of the gases stored in a container.

[Container]

The container in which a fluorobutene is stored may be any container that can store a fluorobutene and be sealed, and the shape, the size, the material, and the like are not specifically limited. The material of the container may be, for example, a metal, ceramics, or a resin. Examples of the metal include manganese steel, stainless steel, Hastelloy (registered trademark), and Inconel (registered trademark).

[Metal Impurity]

The fluorobutene pertaining to the present embodiment contains or does not contain at least one of sodium, potassium, magnesium, and calcium as a metal impurity. The fluorobutene is stored in a container in which the total concentration of sodium, potassium, magnesium, and calcium is 1,000 ppb by mass or less when containing at least one of sodium, potassium, magnesium, and calcium. As described above, this condition suppresses the polymerization reaction of carbon-carbon double bonds in the fluorobutene, and consequently, the fluorobutene is unlikely to be polymerized during storage. In the description, the not containing something means that it cannot be quantified by using an inductively coupled plasma mass spectrometer (ICP-MS).

To suppress polymerization of a fluorobutene during storage, the total concentration of sodium, potassium, magnesium, and calcium in the fluorobutene is required to be 1,000 ppb by mass or less, but is preferably 500 ppb by mass or less and more preferably 100 ppb by mass or less.

To better suppress polymerization of a fluorobutene during storage, each concentration of sodium, potassium, magnesium, and calcium in the fluorobutene is preferably 300 ppb by mass or less and more preferably 100 ppb by mass or less.

The total concentration of sodium, potassium, magnesium, and calcium may be 1 ppb by mass or more.

The concentration of a metal impurity such as sodium, potassium, magnesium, and calcium in a fluorobutene may be quantified by using an inductively coupled plasma mass spectrometer (ICP-MS).

To better suppress polymerization of a fluorobutene during storage, the concentrations of manganese (Mn), cobalt (Co), nickel (Ni), and silicon (Si) are also preferably low, as well as the concentrations of sodium, potassium, magnesium, and calcium, in the fluorobutene.

In other words, a fluorobutene contains or does not contain at least one of sodium, potassium, magnesium, and calcium as a metal impurity, and the total concentration of sodium, potassium, magnesium, and calcium is 1,000 ppb by mass or less when the fluorobutene contains at least one of sodium, potassium, magnesium, and calcium. In addition to this requirement, the fluorobutene further contains or does not contain at least one of manganese, cobalt, nickel, and silicon as the metal impurity, and the fluorobutene is preferably stored with a sum total concentration of sodium, potassium, magnesium, calcium, manganese, cobalt, nickel, and silicon of 2,000 ppb by mass or less when further containing at least one of manganese, cobalt, nickel, and silicon. The fluorobutene is more preferably stored with a sum total concentration of 1,000 ppb by mass or less, and the fluorobutene is even more preferably stored with a sum total concentration of 500 ppb by mass or less.

The sum total concentration of sodium, potassium, magnesium, calcium, manganese, cobalt, nickel, and silicon may be 2 ppb by mass or more.

To further suppress polymerization of a fluorobutene during storage, the concentrations of copper (Cu), zinc (Zn), and aluminum (Al) are also preferably low, as well as the concentrations of sodium, potassium, magnesium, and calcium and the concentrations of manganese, cobalt, nickel, and silicon, in the fluorobutene.

In other words, when a fluorobutene contains at least one of sodium, potassium, magnesium, and calcium and at least one of manganese, cobalt, nickel, and silicon as metal impurities and further contains at least one of copper, zinc, and aluminum as a metal impurity, the fluorobutene is preferably stored with a total concentration of all these metal impurities contained of 3,000 ppb by mass or less, the fluorobutene is more preferably stored with a total concentration of 1,500 ppb by mass or less, and the fluorobutene is even more preferably stored with a total concentration of 1,000 ppb by mass or less.

The above metal impurities may be contained as an elemental metal, a metallic compound, a metal halide, or a metal complex in a fluorobutene. Examples of the form of the metal impurity in a fluorobutene include microparticles, droplets, and gas. Sodium, potassium, magnesium, and calcium are mixed in a fluorobutene supposedly from a material, a reaction vessel, a refiner, or the like used to synthesize the fluorobutene.

[Method for Producing Fluorobutene Containing Metal Impurity at Low Concentration]

A fluorobutene containing metal impurities at low concentrations may be produced by any method, and examples of the method include a method of removing metal impurities from a fluorobutene containing metal impurities at high concentrations. Metal impurities may be removed from a fluorobutene by any method, and a known method may be used. Examples of the method include a method using a filter, a method using an adsorbent, and distillation.

The material of the filter through which a fluorobutene gas selectively passes is preferably a resin and specifically preferably polytetrafluoroethylene to prevent a metal component from mixing with a fluorobutene. The average pore size of the filter is preferably 0.01 μm or more and 30 μm or less and more preferably 0.1 μm or more and 10 μm or less. A filter having an average pore size within the above range can be used to thoroughly remove metal impurities and can allow a fluorobutene gas to pass through at a sufficient flow rate, achieving high productivity.

The flow rate of a fluorobutene gas passing through the filter is preferably 100 mL/min or more and 5,000 mL/min or less and more preferably 300 mL/min or more and 1,000 mL/min or less. When the flow rate of a fluorobutene gas is within the above range, the fluorobutene gas is prevented from reaching a high pressure, and this can reduce the risk of fluorobutene gas leakage. In addition, high productivity can be achieved.

[Pressure Conditions During Storage]

Pressure conditions during storage in the method for storing a fluorobutene pertaining to the present embodiment are not specifically limited as long as a fluorobutene can be sealed and stored in a container, but the pressure is preferably 0.05 MPa or more and 5 MPa or less and more preferably 0.1 MPa or more and 3 MPa or less. When the pressure conditions are within the above range, a fluorobutene can be allowed to pass without humidification through a container that is connected to a dry etching system.

[Temperature Conditions During Storage]

Temperature conditions during storage in the method for storing a fluorobutene pertaining to the present embodiment are not specifically limited, but the temperature is preferably −20° C. or more and 50° C. or less and more preferably 0° C. or more and 40° C. or less. At a temperature of −20° C. or more during storage, a container is unlikely to deform and thus is unlikely to lose the airtightness. This reduces the possibility of oxygen, water, or the like entering the container. If oxygen, water, or the like entered a container, polymerization reaction or decomposition reaction of a fluorobutene could be accelerated. At a temperature of 50° C. or less during storage, polymerization reaction or decomposition reaction of a fluorobutene is suppressed.

[Etching]

The fluorobutene pertaining to the present embodiment can be used as an etching gas. An etching gas containing the fluorobutene pertaining to the present embodiment can be used in both plasma etching with plasma and plasmaless etching without plasma.

Examples of the plasma etching include reactive ion etching (RIE), inductively coupled plasma (ICP) etching, capacitively coupled plasma (CCP) etching, electron cyclotron resonance (ECR) plasma etching, and microwave plasma etching.

In plasma etching, plasma may be generated in a chamber in which a member to be etched is placed, or a plasma generation chamber may be installed separately from a chamber in which a member to be etched is placed (i.e., remote plasma may be used).

EXAMPLES

The present invention will next be described more specifically with reference to examples and comparative examples. Fluorobutenes containing metal impurities at various concentrations were prepared. Fluorobutene preparation examples will be described below.

Preparation Example 1

A manganese steel tank having a volume of 10 L and four manganese steel cylinders each having a volume of 1 L were prepared. These cylinders are called cylinder A, cylinder B, cylinder C, and cylinder D. The tank was filled with 5,000 g of 1,1,1,4,4,4-hexafluoro-2-butene (boiling point: 9° C.) and was cooled at 0° C. for liquefaction, and a liquid phase portion and a gas phase portion were formed at about 100 kPa. The cylinders A, B, C, and D were depressurized to 1 kPa or less by using a vacuum pump and then were cooled to −78° C.

From the upper outlet where the gas phase portion was present in the tank, 500 g of 1,1,1,4,4,4-hexafluoro-2-butene gas was extracted, allowed to pass through a filter, and collected in the cylinder A at a reduced pressure. The filter was a PTFE filter manufactured by Flon Industry and having an outer diameter of 50 mm, a thickness of 80 μm, and an average pore size of 0.3 μm. The flow rate of the gas passing through the filter was adjusted to 500 mL/min by using a mass flow controller. The amount of 1,1,1,4,4,4-hexafluoro-2-butene gas collected in the cylinder A was 492 g.

The 1,1,1,4,4,4-hexafluoro-2-butene collected in the cylinder A is regarded as sample 1-1. The 1,1,1,4,4,4-hexafluoro-2-butene gas collected in the cylinder A was extracted from the upper outlet, and the concentrations of various metal impurities were determined by using an inductively coupled plasma mass spectrometer. The results are shown in Table 1.

TABLE 1

| | Na | K | Mg | Ca | Total | Mn | Co | Ni | Si | Total |
|---|---|---|---|---|---|---|---|---|---|---|
| Sample 1-1 | 5 | 3 | 1 | 3 | 12 | — | — | — | — | — |
| Sample 1-2 | 22 | 19 | 17 | 19 | 77 | — | — | — | — | — |
| Sample 1-3 | 214 | 208 | 171 | 178 | 771 | 184 | 163 | 199 | 232 | 778 |
| Sample 1-4 | 443 | 428 | 359 | 387 | 1617 | — | — | — | — | — |

*) The unit of numerical values is ppb by mass.
"—" means no measurement data.

Next, the temperature of the cylinder A was raised to about 0° C., and a liquid phase portion and a gas phase portion were formed. From the upper outlet where the gas phase portion was present in the cylinder A, 100 g of 1,1,1,4,4,4-hexafluoro-2-butene gas was extracted and transferred to the cylinder B at a reduced pressure. From the tank, 10 g of 1,1,1,4,4,4-hexafluoro-2-butene gas was extracted and transferred to the cylinder B at a reduced pressure. The temperature of the cylinder B was then raised to room temperature and was allowed to stand for 24 hours. The 1,1,1,4,4,4-hexafluoro-2-butene after standing is regarded as sample 1-2. From the upper outlet where the gas phase portion was present in the cylinder B after standing, the 1,1,1,4,4,4-hexafluoro-2-butene gas was extracted, and the concentrations of various metal impurities were determined by using an inductively coupled plasma mass spectrometer. The results are shown in Table 1.

In a similar manner, from the upper outlet where the gas phase portion was present in the cylinder A, 100 g of 1,1,1,4,4,4-hexafluoro-2-butene gas was extracted and transferred to the cylinder C at a reduced pressure. From the tank, 100 g of 1,1,1,4,4,4-hexafluoro-2-butene gas was extracted and transferred to the cylinder C at a reduced pressure. The temperature of the cylinder C was then raised to room temperature and was allowed to stand for 24 hours. The 1,1,1,4,4,4-hexafluoro-2-butene after standing was regarded as sample 1-3. From the upper outlet where the gas phase portion was present in the cylinder C after standing, the 1,1,1,4,4,4-hexafluoro-2-butene gas was extracted, and the concentrations of various metal impurities were determined by using an inductively coupled plasma mass spectrometer. The results are shown in Table 1.

In a similar manner, from the upper outlet where the gas phase portion was present in the cylinder A, 100 g of 1,1,1,4,4,4-hexafluoro-2-butene gas was extracted and transferred to the cylinder D at a reduced pressure. From the tank, 200 g of 1,1,1,4,4,4-hexafluoro-2-butene gas was extracted and transferred to the cylinder D at a reduced pressure. The temperature of the cylinder D was then raised to room temperature and was allowed to stand for 24 hours. The 1,1,1,4,4,4-hexafluoro-2-butene after standing was regarded as sample 1-4. From the upper outlet where the gas phase portion was present in the cylinder D after standing, the 1,1,1,4,4,4-hexafluoro-2-butene gas was extracted, and the concentrations of various metal impurities were determined by using an inductively coupled plasma mass spectrometer. The results are shown in Table 1.

Preparation Example 2

The same procedure as in Preparation Example 1 was performed except that 1,1,1,2,4,4,4-heptafluoro-2-butene was used as a fluorobutene, and samples 2-1 to 2-4 were prepared. The concentrations of various metal impurities in each sample were determined by using an inductively coupled plasma mass spectrometer. The results are shown in Table 2.

TABLE 2

| | Na | K | Mg | Ca | Total | Mn | Co | Ni | Si | Total |
|---|---|---|---|---|---|---|---|---|---|---|
| Sample 2-1 | 3 | 3 | 2 | 3 | 11 | — | — | — | — | — |
| Sample 2-2 | 21 | 21 | 15 | 19 | 76 | — | — | — | — | — |
| Sample 2-3 | 218 | 210 | 168 | 171 | 767 | 191 | 167 | 189 | 222 | 769 |
| Sample 2-4 | 418 | 415 | 332 | 369 | 1534 | — | — | — | — | — |

*) The unit of numerical values is ppb by mass.
"—" means no measurement data.

Preparation Example 3

The same procedure as in Preparation Example 1 was performed except that 3,3,4,4,4-pentafluoro-1-butene was used as a fluorobutene, and samples 3-1 to 3-4 were prepared. The concentrations of various metal impurities in each sample were determined by using an inductively coupled plasma mass spectrometer. The results are shown in Table 3.

TABLE 3

| | Na | K | Mg | Ca | Total | Mn | Co | Ni | Si | Total |
|---|---|---|---|---|---|---|---|---|---|---|
| Sample 3-1 | 4 | 2 | 2 | 4 | 12 | — | — | — | — | — |
| Sample 3-2 | 23 | 21 | 16 | 18 | 78 | — | — | — | — | — |
| Sample 3-3 | 219 | 206 | 173 | 178 | 776 | 210 | 191 | 200 | 241 | 842 |
| Sample 3-4 | 428 | 417 | 344 | 353 | 1542 | — | — | — | — | — |

*) The unit of numerical values is ppb by mass.
"—" means no measurement data.

Preparation Example 4

The same procedure as in Preparation Example 1 was performed except that 2,3,3,4,4,4-hexafluoro-1-butene was used as a fluorobutene, and samples 4-1 to 4-4 were prepared. The concentrations of various metal impurities in each sample were determined by using an inductively coupled plasma mass spectrometer. The results are shown in Table 4.

TABLE 4

| | Na | K | Mg | Ca | Total | Mr | Co | Ni | Si | Total |
|---|---|---|---|---|---|---|---|---|---|---|
| Sample 4-1 | 5 | 3 | 1 | 4 | 13 | — | — | — | — | — |
| Sample 4-2 | 25 | 22 | 18 | 20 | 85 | — | — | — | — | — |
| Sample 4-3 | 233 | 218 | 193 | 202 | 846 | 197 | 184 | 204 | 237 | 822 |
| Sample 4-4 | 452 | 437 | 383 | 399 | 1671 | — | — | — | — | — |

*) The unit of numerical values is ppb by mass.
"—" means no measurement data.

Example 1

The cylinder A was allowed to stand at 20° C. for 30 days, and then from the gas phase portion of the cylinder A, 1,1,1,4,4,4-hexafluoro-2-butene gas was extracted and analyzed by gas chromatography to quantify the concentration of the dimer of 1,1,1,4,4,4-hexafluoro-2-butene in sample 1-1. As a result, no dimer was detected.

Measurement conditions of the gas chromatography were as follows:

Gas chromatograph: GC-2014 manufactured by Shimadzu Corporation

Column: carbopackB_1% sp-1000

Injection temperature: 200° C.

Column temperature: 100° C.

Detector: FID

Detector temperature: 200° C.

Carrier gas: helium

Detection limit: 1 ppm by mass

Examples 2 to 12 and Comparative Examples 1 to 4

Analysis objects and analysis results in Examples 2 to 12 and Comparative Examples 1 to 4 are shown in Table 5 in comparison with those in Example 1. In other words, substantially the same analysis as in Example 1 was performed except the items shown in Table 5.

TABLE 5

| | Sample/cylinder | Fluorobutene | Dimer concentration (ppm by mass) | Result |
|---|---|---|---|---|
| Ex. 1 | 1-1/A | 1,1,1,4,4,4-Hexafluoro-2-butene | Not detected | (−) |
| Ex. 2 | 1-2/B | " | Not detected | (−) |
| Ex. 3 | 1-3/C | " | Not detected | (−) |
| Comp. Ex. 1 | 1-4/D | " | 61 | (+) |
| Ex. 4 | 2-1/A | 1,1,1,2,4,4,4-Heptafluoro-2-butene | Not detected | (−) |
| Ex. 5 | 2-2/B | " | Not detected | (−) |
| Ex. 6 | 2-3/C | " | Not detected | (−) |
| Comp. Ex. 2 | 2-4/D | " | 78 | (+) |
| Ex. 7 | 3-1/A | 3,3,4,4,4-Pentafluoro-1-butene | Not detected | (−) |
| Ex. 8 | 3-2/B | " | Not detected | (−) |
| Ex. 9 | 3-3/C | " | Not detected | (−) |
| Comp. Ex. 3 | 3-4/D | " | 53 | (+) |
| Ex. 10 | 4-1/A | 2,3,3,4,4,4-Hexafluoro-1-butene | Not detected | (−) |
| Ex. 11 | 4-2/B | " | Not detected | (−) |
| Ex. 12 | 4-3/C | " | Not detected | (−) |
| Comp. Ex. 4 | 4-4/D | " | 77 | (+) |

(−): No polymerization progress was observed.
(+): Polymerization progress was observed.

The invention claimed is:

1. A method for storing a fluorobutene represented by general formula $C_4H_xF_y$ where x is 0 or more and 7 or less, y is 1 or more and 8 or less, and x+y is 8, wherein the fluorobutene contains or does not contain at least one of sodium, potassium, magnesium, and calcium as a metal impurity, and the fluorobutene is stored in a container in which a total concentration of sodium, potassium, magnesium, and calcium is 1,000 ppb by mass or less when the fluorobutene contains at least one of sodium, potassium, magnesium, and calcium.

2. The method for storing a fluorobutene according to claim 1, wherein the fluorobutene further contains or does not contain at least one of manganese, cobalt, nickel, and silicon as the metal impurity, and the fluorobutene is stored in a container in which a total concentration of sodium, potassium, magnesium, calcium, manganese, cobalt, nickel, and silicon is 2000 ppb by mass or less when the fluorobutene further contains at least one of manganese, cobalt, nickel, and silicon.

3. The method for storing a fluorobutene according to claim 1, wherein the fluorobutene is at least one selected from 1,1,1,4,4,4-hexafluoro-2-butene, 1,1,1,2,4,4,4-heptafluoro-2-butene, 3,3,4,4,4-pentafluoro-1-butene, and 2,3,3,4,4,4-hexafluoro-1-butene.

4. The method for storing a fluorobutene according to claim 1, wherein the fluorobutene is stored at a temperature of −20° C. or more and 50° C. or less.

5. The method for storing a fluorobutene according to claim 2, wherein the fluorobutene is at least one selected from 1,1,1,4,4,4-hexafluoro-2-butene, 1,1,1,2,4,4,4-heptafluoro-2-butene, 3,3,4,4,4-pentafluoro-1-butene, and 2,3,3,4,4,4-hexafluoro-1-butene.

6. The method for storing a fluorobutene according to claim 2, wherein the fluorobutene is stored at a temperature of −20° C. or more and 50° C. or less.

7. The method for storing a fluorobutene according to claim 3, wherein the fluorobutene is stored at a temperature of −20° C. or more and 50° C. or less.

* * * * *